(12) United States Patent
Curiel et al.

(10) Patent No.: US 8,944,811 B2
(45) Date of Patent: Feb. 3, 2015

(54) METHOD FOR PRODUCING A CUSTOMIZED ORTHODONTIC DEVICE

(75) Inventors: Patrick Curiel, Neuilly sur Seine (FR); Daniel Julie, Marseilles (FR)

(73) Assignee: H 32, Paris (FR)

( * ) Notice: Subject to any disclaimer, the term of this patent is extended or adjusted under 35 U.S.C. 154(b) by 836 days.

(21) Appl. No.: 12/740,354

(22) PCT Filed: Oct. 31, 2008

(86) PCT No.: PCT/FR2008/051970
§ 371 (c)(1), (2), (4) Date: Jan. 13, 2011

(87) PCT Pub. No.: WO2009/056776
PCT Pub. Date: May 7, 2009

(65) Prior Publication Data
US 2011/0097682 A1   Apr. 28, 2011

(30) Foreign Application Priority Data

Oct. 31, 2007   (FR) ...................................... 07 07686

(51) Int. Cl.
*A61C 3/00* (2006.01)
*A61C 7/14* (2006.01)
*A61C 7/00* (2006.01)

(52) U.S. Cl.
CPC . *A61C 7/14* (2013.01); *A61C 7/145* (2013.01); *A61C 7/002* (2013.01); *A61C 7/146* (2013.01)
USPC .......................... 433/2; 433/8; 433/20; 700/98

(58) Field of Classification Search
USPC ............................ 433/8–20, 24, 2; 700/97–98
See application file for complete search history.

(56) References Cited

U.S. PATENT DOCUMENTS

| | | | |
|---|---|---|---|
| 3,477,128 A | | 11/1969 | Andrews |
| 5,368,478 A | * | 11/1994 | Andreiko et al. ................ 433/24 |
| 5,533,895 A | * | 7/1996 | Andreiko et al. ................ 433/24 |
| 6,264,468 B1 | * | 7/2001 | Takemoto ........................... 433/8 |
| 6,776,614 B2 | * | 8/2004 | Wiechmann et al. ........... 433/24 |
| 7,811,087 B2 | * | 10/2010 | Wiechmann et al. ............. 433/9 |

(Continued)

FOREIGN PATENT DOCUMENTS

| | | |
|---|---|---|
| EP | 0 696 444 A2 | 2/1996 |
| EP | 1 080 697 A1 | 3/2001 |

(Continued)

OTHER PUBLICATIONS

International Search Report, dated Jun. 3, 2009, from corresponding PCT application.

(Continued)

*Primary Examiner* — Cris L Rodriguez
*Assistant Examiner* — Hao D Mai
(74) *Attorney, Agent, or Firm* — Andrus Intellectual Property Law, LLP

(57) ABSTRACT

A customized orthodontic device for the treatment of a patient and a method for producing the same. The customized orthodontic device includes a plurality of bracket assemblies which each include a bracket with at least one groove. The groove is configured to receive an arch wire. The bracket assemblies are digitally designed to include the bracket, a base, and an intermediate component. The base is configured to be placed on a face of a tooth. The intermediate component extends between the bracket and the base.

13 Claims, 2 Drawing Sheets

(56) References Cited

U.S. PATENT DOCUMENTS

Figure 1:
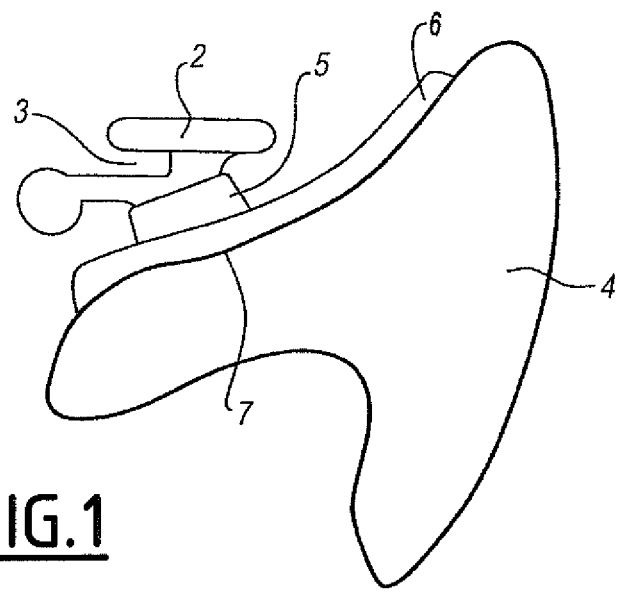

| | | | |
|---|---|---|---|
| 8,057,226 B2 * | 11/2011 | Wiechmann et al. | 433/16 |
| 8,147,243 B2 * | 4/2012 | Wiechmann | 433/9 |
| 2003/0152884 A1 * | 8/2003 | Wiechmann et al. | 433/9 |
| 2004/0029068 A1 | 2/2004 | Sachdeva et al. | |
| 2004/0214129 A1 | 10/2004 | Sachdeva et al. | |
| 2004/0219473 A1 * | 11/2004 | Cleary et al. | 433/9 |
| 2006/0079981 A1 * | 4/2006 | Rubbert et al. | 700/98 |
| 2007/0092849 A1 * | 4/2007 | Cosse | 433/8 |

FOREIGN PATENT DOCUMENTS

| | | |
|---|---|---|
| EP | 1 702 582 A2 | 9/2006 |
| WO | 94/10935 A1 | 5/1994 |
| WO | 03/068099 A2 | 8/2003 |

OTHER PUBLICATIONS

European Office Action dated Mar. 21, 2013 for Appln. No. 08 845 858.3.

* cited by examiner

METHOD FOR PRODUCING A CUSTOMIZED ORTHODONTIC DEVICE

The invention relates to a method for producing, for the treatment of a patient, a customised orthodontic device which is intended to be used primarily, but not exclusively, for a lingual technique, that is to say, with the device arranged on the posterior non-visible face of the teeth.

Conventionally, such devices comprise:

at least one arch wire, otherwise referred to as a metal wire, which applies to the teeth a force which tends to move them, from their initial unsatisfactory position, referred to as the "incorrect position", to a final satisfactory position, referred to as the "corrected position";

and a series of fasteners, also generally referred to as "brackets", each provided with at least one groove for receiving an arch wire; these brackets are fixed individually to the teeth of the patient, in a predetermined position which allows the arch wire to transfer to the teeth the forces required for them to move from the incorrect position to the corrected position during the treatment.

Most commonly, one or more arch wires are used in conjunction with a single series of brackets each comprising one or more grooves.

Lingual orthodontic techniques, which have the aesthetic advantage of leaving the device practically invisible from the outer side, began to be developed around 1980. At this time, however, they were based on entirely manual design and production of the devices, and were very complex to use. An important element in the success of the treatment is the correct positioning of the bracket and the groove thereof on the tooth, since this positioning determines the orientation of the forces which are applied to the corresponding tooth and therefore the orientations of the tooth in the various spatial directions when it is in the final corrected position. This positioning is much more complex to carry out using a lingual technique than using a technique referred to as a labial or vestibular technique (where the device is arranged on the anterior face of the teeth) owing to the significant angulation of the posterior faces of the teeth. Owing to this angulation, a slight positioning error of the bracket may place the groove in an incorrect position which is incapable of ensuring the desired correction of the position of the tooth.

An improvement of this technique has been brought about with the system referred to as "C.L.A.S.S.". It involves producing two plaster mouldings of an impression of the arch and the incorrectly positioned teeth of the patient. One of these mouldings is retained, the other is used by the technician to produce a model of the arch with the teeth in the final corrected position. To this end, the teeth of the moulding are cut one by one and repositioned in the corrected positions (a step generally referred to as "set-up"). Then, the technician places brackets of standardised shape on a series of pre-existing templates which appear to him to be best suited to the inner curvature of the teeth in the predetermined zones of the arch (for example, facing the incisors, facing each of the canines, facing each of the series of premolars and facing each of the series of molars), and moves these template/bracket assemblies towards the teeth of the moulding. The result is that one or some of the brackets can be supported directly on the teeth of the moulding but that empty spaces exist between the other brackets and the other teeth. These empty spaces are filled with adhesive in order to fix the brackets in position. A photocopy is then made of the moulding with the brackets in place, from which the shape of the arch wire is determined which will be required to place the teeth in the corrected position. Then, the brackets are partially enclosed in small shells of resin, they are placed on the teeth of the moulding in the incorrect position using retention devices and a transfer key of the entire arch is made from silicone, by means of which it is possible to carry out, in a single operation, the simultaneous transfer by means of adhesive-bonding of all the brackets to the incorrectly positioned teeth of the patient. The arch wire having the required shape is then placed in the grooves of the brackets, in which it is then blocked by closing the inlet of the groove to prevent it from becoming loose, and the treatment can begin.

However, this technique has a number of disadvantages. The mass of adhesive-bonding agent, with which the empty space between the bracket and the corresponding tooth thereof is filled and the connection between the bracket and the tooth is ensured during treatment, can be sized only in a relatively approximate manner. The material thereof is susceptible to ageing and losing its mechanical characteristics which would allow it to correctly perform its function in repositioning the teeth. If this material becomes broken, it is not possible to restore it to its initial shape, which is in principle ideal. The use of pre-existing templates and retention devices, which therefore have standardised dimensions, results in the positionings of the brackets which they allow to be produced not always being ideally adapted to the precise morphology of the arch of the patient. Generally, this method requires very significant production time and extremely qualified and meticulous technicians to implement it under the best conditions in order to obtain the best desired results. Its use is therefore very costly and restrictive for the patient.

Data-processing techniques have enabled significant improvements in the ease of designing customised orthodontic devices, specific to each patient.

In particular document WO-A-03/068099 teaches designing in a customised manner an assembly formed on the one hand by the virtual image of a base for fixing to the tooth, designed digitally from a data-processing image of the arch of the patient with the teeth in an incorrect position and, on the other hand, a virtual image of a bracket which is provided with a groove for inserting the arch wire, this image being taken from a virtual library of brackets of predetermined shapes. There is then produced a bracket which is formed by a single body which results from the combination of these two images. Then, an arch wire is designed so as to be shaped using a specific device which is intended to connect the brackets and move the teeth of the patient into the corrected position. This arch wire inevitably has a complex shape, in particular since it is constituted by a series of multiple zones having different radii of curvature, which is required for connecting the brackets, and generally extends in the three spatial dimensions.

The disadvantages of this technique are principally as follows. Since the body which forms both the base fixed to the tooth and the bracket which carries the groove for inserting the arch wire is designed and produced by means of rapid prototyping, it is difficult to produce improved fastening systems with regard to the shape of the brackets. In particular, it is difficult to use brackets in which a system is structurally integrated for blocking the arch wire by means of clip-fitting or the like, referred to as "self-ligating brackets". This type of bracket, which is used more and more frequently, appears to be a significant element in the complete success of the treatment. Furthermore, the shaping of the arch wire, owing to its complexity, must be produced in an automated manner, with materials which have precise characteristics so that they can take on and retain this shaping. And, if a modification of the shape of the arch wire appears necessary at the beginning of or during the treatment, it is not possible to carry this out without changing the whole of the arch wire. The modularity of the device is therefore limited. Finally, the substantial sinuous nature of the arch wire which, as set out, can generally extend substantially in three spatial dimensions, significantly limits its possibilities of sliding inside the grooves of the brackets, whilst this possibility of sliding would be advantageous to the effective implementation of the treatment to accompany the movement of the teeth as far as their corrected position.

The object of the invention is to provide a method for designing an orthodontic device and a resulting device which solves, better than the existing methods, with much greater ease of implementation and at a lower cost, the technical problems set out above, in particular for treatments involving lingual techniques.

To this end, the invention relates to a method for producing a customised orthodontic device for the treatment of a patient, the device comprising at least one treatment arch wire and a plurality of elements which each comprise a bracket which is provided with at least one groove, into which the arch wire can be inserted, each bracket being intended to be placed on an intermediate component which is itself intended to be placed on a base which is intended to be placed on an anterior or posterior face of a tooth, the method making provision for the brackets, intermediate components and bases to be digitally designed in a customised manner after having formed a representation in the corrected position of the arch and the faces of the teeth, to which the bases must be fixed, characterised in that:

a model arch wire is positioned relative to the faces of the teeth on the representation, the geometry of the structural arch wire member being homothetic with that of the arch wire;

and the elements are digitally designed so as to give them a shape which corresponds to the geometry of the space which, following the orthodontic treatment, would separate the tooth and the treatment curved member when the tooth had assumed its corrected position and the arch wire had returned to its initial shape.

The model arch wire may have the same shape and dimensions as the treatment arch wire or be constituted by this treatment arch wire itself.

The treatment arch wire may extend in a single plane.

The arch wire may be composed of a single portion having a substantially continuous curvature, or a series of portions which each have substantially continuous curvature.

During the digital design of the elements, it is possible to design the base so that it has a support face which complements that of the portion of the face of the tooth on which it must be placed.

During the digital design of the elements, it is possible to carry out a merging of at least two components from the brackets, the intermediate components and the bases which are intended to be fitted to specific teeth, with a view to subsequent production of the elements.

It is thus possible to carry out the merging of two portions from the brackets, the intermediate components and the bases in order to digitally obtain a merged component, and to provide means for assisting the positioning of the remaining component on the merged component.

The assistance means may be constituted by male-female shapes provided at the interfaces of the components to be fixed to each other.

It is further possible to produce a transfer channel which at least partially surrounds each bracket and the corresponding intermediate component to transfer the device to the arch of the patient.

The representation of the arch and the faces of the teeth of the patient can be obtained by means of three-dimensional digitisation of a model of the arch of the teeth of the patient in the corrected position.

The device may be intended to be placed in a lingual position.

The invention also relates to a customised orthodontic device for the treatment of a patient, the device comprising at least one treatment arch wire and a plurality of elements which each comprise a bracket which is provided with at least one groove, in which the arch wire can be inserted, each bracket being intended to be placed on an intermediate component which is itself intended to be placed on a base which is intended to be placed on an anterior or posterior face of a tooth, characterised in that it has been produced using the above method.

The treatment arch wire may extend in a single plane (P).

It may be constituted by a series of portions which each have substantially continuous curvature, or by a single portion having substantially continuous curvature.

Preferably, at least one of the brackets may be of the self-ligating type.

As will be appreciated, the invention is based on the combined use:

of the formation using a digital method, individually for each tooth, of an assembly formed by a base which conforms to the shape of the face of the tooth to which it will be fixed, of a bracket which is provided with a groove in which an arch wire will be inserted, and an intermediate portion between the base and the bracket whose geometry corresponds to the space which, without it, would be left free at the end of the treatment between the corresponding tooth in the corrected position thereof and the arch wire which will have returned to its initial shape; this assembly can be produced in the form of a single component which includes all the components which have been set out above, or in the form of two or three separate components which are then fixed to each other;

and of an arch wire whose shape and dimensions can be standardised, having substantially continuous curvature with the possible exception of zones which correspond, for example, as illustrated in the Figures, to the transition between teeth or groups of teeth of different types (for example, between canines and premolars and/or between premolars and molars), and which define a series of portions, which each have substantially continuous curvature. In any case, this curved member has not been subjected to a complex shaping operation which is intended to adjust the shape thereof in a fine manner with respect to each of the teeth of the patient.

Therefore, the arch wire may be of the known type referred to as "straight wire" which extends in a single plane and which is produced in accordance with standardised models.

Figure 2:
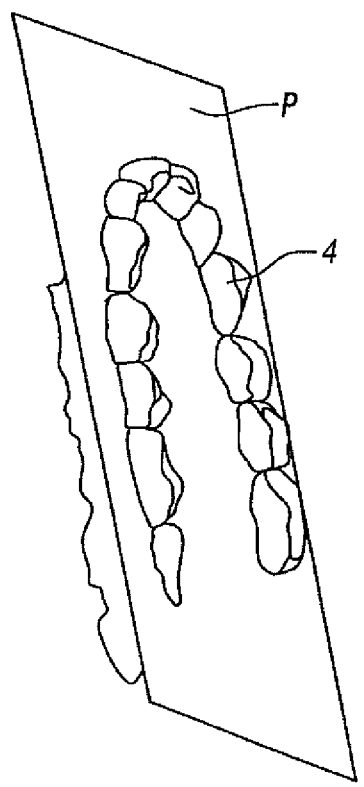
Figure 3:
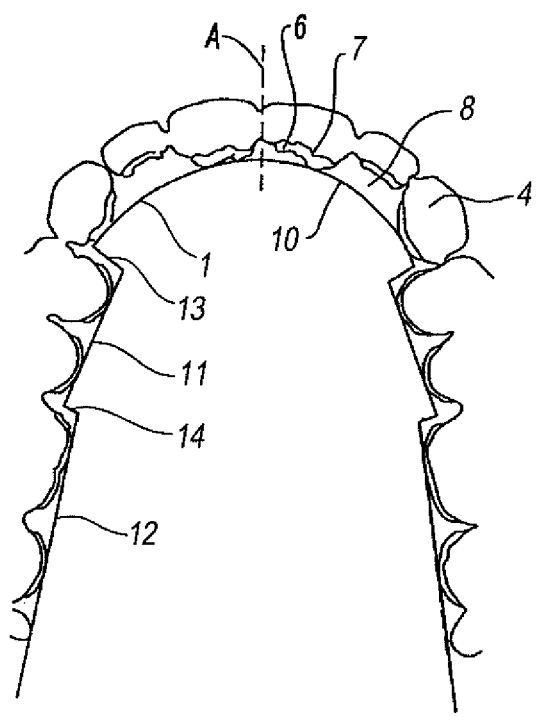
Figure 4:
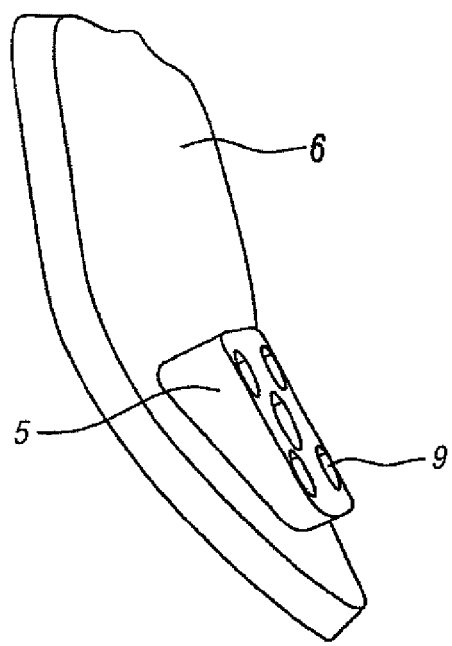
Figure 5:
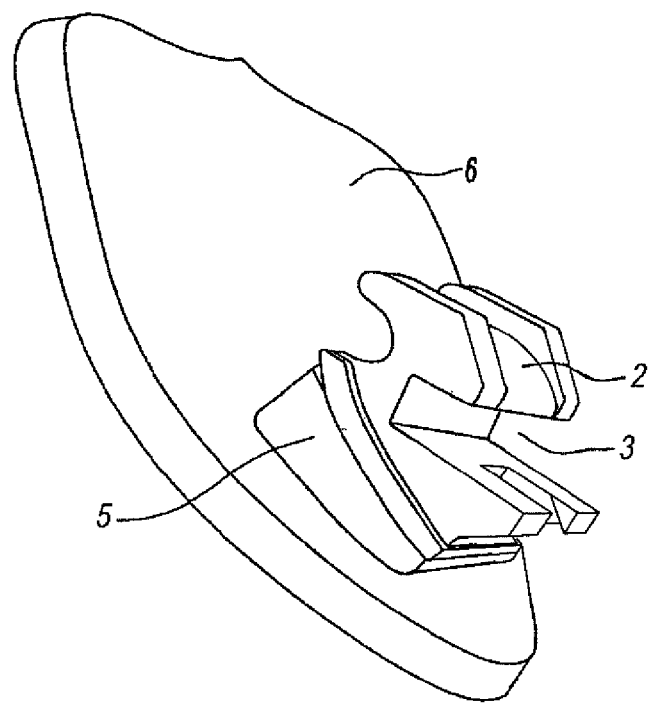

The invention will be better understood from a reading of the following description, given with reference to the following appended Figures, in which:

FIG. 1 is a profile view of a tooth, at the posterior non-visible face of which a bracket is fixed to a base which is itself fixed to the tooth by means of a fixing component, in accordance with an embodiment of the invention;

FIGS. 2 and 3 which are a perspective view (FIG. 2) and a sectional plan view (FIG. 3) in the plane P of FIG. 2 of the corrected position of the teeth of an arch, a model arch wire being positioned in FIG. 3 in plane P relative to the bases which are in a position for fixing to the representation;

FIG. 4 which illustrates the step of adapting the intermediate component for fixing to the base, the component being positioned on the base;

FIG. 5 which is a perspective view of the assembly formed by the base, the fixing component and a bracket which is associated therewith.

An example of a method for producing a customised orthodontic device according to the invention will now be described. The device comprises an arch wire 1 and a plurality of brackets 2, equal in number to the number of teeth for which it is desirable to correct the position, the brackets 2 each being provided with a groove 3 in which the arch wire 1 can be inserted in conventional manner. In this manner, the resilience of the arch wire 1 which tends to make it return to its initial shape, allows a force to be applied to each tooth 4 which tends to move it into its desired corrected position. This force is transmitted to the tooth 4 by means of the bracket 2, an intermediate component 5 which is fixed to the bracket 2 and a base 6 which is fixed on the one hand to the posterior face 7 of the tooth 4 and on the other hand to the intermediate component 5.

It will be appreciated that the following description is based on an embodiment of the invention in the context of a lingual technique, therefore with the device located at the normally non-visible posterior side of the teeth 4. However, given evident adaptations by the person skilled in the art, the same method according to the invention can be used to produce devices in accordance with a labial/vestibular technique, that is to say, in which the brackets and the arch wire are placed on the visible anterior face of the teeth 4. In the same manner, the person skilled in the art will be able to adapt the method to the case in which more than one arch wire may be used on the same arch, which would involve each bracket 2 comprising a plurality of grooves 3, or each tooth 4 being provided with a plurality of brackets 2 for receiving a plurality of arch wires 1.

In order to allow the orthodontic treatment to be carried out, the positioning of the bracket 2 and, in particular, the groove 3 thereof, must be determined in order to make the arch wire 1 apply the force required to move the tooth 4 in an incorrect position towards its intended corrected position. The sizing of the assembly formed by the bracket 2, the intermediate component 5 and the base 6 must also be determined to this end. This leads to the design and the production of these assemblies being customised but, in accordance with one of the advantages of the invention, possibly without the initial geometry of the arch wire 1 deviating from a standardised shape, defined in a plane, and not requiring complex shaping of the arch wire 1 before it is inserted in the brackets 2.

To this end, according to the invention, the elements are digitally designed, and in particular each intermediate component 5, in order to make them have a shape which corresponds to the geometry of the space 8 which, following the orthodontic treatment, would separate the posterior face 7 of the tooth 4 and the arch wire 1 when the tooth 4 had assumed the corrected position thereof and the arch wire 1 had returned to its initial shape. In this manner, in particular, the thickness of the intermediate component 5 is defined, in accordance with the precise morphology of the corresponding tooth 4, in order to compensate for the differences in thickness and orientations of the teeth 4 of the patient in different spatial directions, so that no prior modification of the shape of the arch wire 1 is required to carry out the alignment of the teeth 4 in their corrected position. Also, the digital design of the various components preferably allows an alignment of the grooves 3 of the brackets 2 to be readily achieved in the same plane so that the arch wire 1 does not need to be deformed to confer thereon a distorted shape (that is to say, not defined in a plane P illustrated in FIG. 2). It is therefore possible to design the whole with a view to using arch wires having simple shapes and standard dimensions, the adaptation to the specific case of the patient being carried out in particular owing to the fine sizing of the intermediate components 5.

In one embodiment of the invention, during the digital design and the production, the base 6, the intermediate component 5 and the bracket 2 are merged into one component which is produced by casting in a mould. The advantage of this technique is that the digital fusion is simple to carry out when the device is designed and allows at this stage the shape of the portion of the component which acts as the bracket 2 to be modified in order to best adapt it to the morphological requirements of the patient. However, production by means of casting in a mould requires the bracket portion 2 to have a relatively simple shape which may exclude the use of some geometries of self-ligating brackets which would be advantageous as set out above.

In another embodiment of the invention, the brackets 2, the intermediate components 5 and the bases 6 are produced separately then fixed to each other, for example, by means of welding, adhesive-bonding or clip-fitting. It is then possible to use brackets 2 of the standardised type, which may, for example, be identical for each group of teeth 4. Since the brackets can be produced using methods other than casting in a mould, for example, machining, they may have complex and precise shapes, which allows in particular, the self-ligating devices to be more readily used for retaining the arch wire 1 in the grooves 3. In the same manner, the intermediate components 5 and the bases 6 can be produced using methods other than moulding: machining, sintering, or rapid prototyping. This variant, if it is correctly implemented, may lead to the production of devices which are more effective than the previous one. The production time and cost of the device are, however, higher than in the previous variant in which all the functional elements are merged into a single component. Furthermore, the fixing of the elements to each other is likely to introduce occurrences of imprecision in their relative positioning operations. However, one way of overcoming this disadvantage is to provide on each element, during its digital design, means for assisting these positionings, such as male-female shapes which are provided on the contact surfaces thereof. They may take the shape, as can be seen in FIG. 4, of housings 9 provided in one of the elements (in this instance, the intermediate component 5) and pins corresponding to these housings provided on the element which must be welded to the preceding element (in this instance, the pins are provided on the lower face of the bracket 2 which cannot be seen in the Figures). Geometries other than housing/pin systems can be envisaged, such as corrugations having complementary shapes. These positioning means can be provided not only at the interfaces between the brackets 2 and the intermediate components 5 but also at the interfaces between the intermediate components 5 and the bases 6.

In other embodiments, it is possible to combine the two preceding embodiments, by merging only two of the three portions of the elements which are intended for specific teeth 4 during the digital design, that is to say:

either the base 6 and the intermediate component 5, the bracket 2 being designed and produced separately therefrom, then fixed to the intermediate component 5;

either the intermediate component 5 and the bracket 2, the base 6 being designed and produced separately then fixed to the intermediate component 5.

In the same manner as that described above, means for assisting the relative positioning of the portions to be fixed to each other can be provided where they would be advantageous.

Of course, in the same device, it is possible to use on the various teeth 4 elements whose portions have been integrally merged during their design and/or elements in which two portions have been merged and/or elements in which no portion has been merged.

The various elements and/or the various portions thereof are designed based on a three-dimensional digitisation of a model of the teeth 4 of the patient in the corrected position, produced in accordance with the conventional techniques previously described, for example, moulding of the arch of the teeth 4 in the incorrect position, then cutting and moving the teeth 4 into the corrected position in order to form the model. After digitisation, the representation of the model is transferred into an item of software for processing three-dimensional images for implementing the remainder of the method. In a variant, however, the representation of the teeth 4 in the corrected position can be obtained using purely digital means, based on a digitisation of the teeth 4 of the patient in the incorrect position, the result of which is processed by an appropriate item of software in order to arrive at the representation of the arch in the corrected position.

It is possible to make provision for the arch wire 1 to be able to be placed in almost direct abutment against specific teeth 4, that is to say, without using an intermediate component 5 between the bracket 2 and the base 6 if that is found to be possible in view of the digital design of the device. In this instance, the base 6 itself is what acts as the intermediate component 5, and the face thereof opposite the one which is in contact with the tooth 4 can consequently be shaped to conform to the bracket 2.

As has been set out, this arch wire 1 may advantageously extend in a single plane P and have either a substantially continuous curvature over the entire length thereof (therefore be of the type referred to as "straight wire") or, as illustrated in FIG. 3, a series of portions 10, 11, 12 which themselves have a substantially continuous curvature and which are connected by a small number of transition zones 13, 14 in order to allow the arch wire 1 to move as close as possible to the various teeth 4 of the patient when they are in the corrected position. This configuration allows the thickness of at least some of the intermediate components 5 to be minimised, and therefore the general size of the device. Better comfort is thus provided for the patient during treatment. Generally, this arch wire 1 has a symmetry relative to the longitudinal centre axis (A) of the arch in the corrected position.

After the elements of the device which are intended to be fixed to the teeth of the patient have been produced according to one of the techniques in accordance with the invention, it is possible to provide a transfer channel, for example, of silicone, which at least partially surrounds each of the elements. To this end, it is possible to place the elements on a model of the arch of the teeth of the patient in the incorrect position, produced, for example, from a moulding of the arch. This positioning is ensured using a soluble adhesive agent or any other system which allows the elements to be readily detached. The correct nature of this positioning can be verified using at this stage an arch wire referred to as a "model arch wire", which is placed in the grooves 3 of the brackets 2. This arch wire has a geometry which is homothetic with that of the arch wire 1 which will be used during the treatment, or strictly identical to this geometry. Optionally, this model arch wire is an arch wire which is identical to the arch wire 1 which will be used during the treatment, or the arch wire 1 itself, which is therefore used as a model arch wire. In this instance, the homothetic relationship between the model arch wire and the treatment arch wire 1 is quite simply equal to 1. This is illustrated in FIG. 3.

A precise model is thus obtained of what the device will be after it is placed on the arch of the patient and it is possible to carry out any rectifications which may be required. Then, the channel is produced by means of moulding, the moulding integrating the elements. The channel is then detached from the model and transferred to the arch of the patient, to the teeth 4 of which the elements are conventionally fixed by means of adhesive-bonding, in a single operation, without any risk of a positioning error. Then, the channel is detached from the elements and the arch wire 1 is placed and blocked in the grooves 3 of the brackets 2 using conventional means, preferably integrated in the brackets 2 which are referred to as being "self-ligating".

The invention claimed is:

1. A method for producing a customized orthodontic device for treatment of a patient, the device comprising a plurality of bracket assemblies each of which comprise a bracket which is provided with at least one groove, a base configured to be placed on a face of a tooth, and an intermediate component that extends between the bracket and the base, the method comprising:
   obtaining a digital representation of a dentition of the patient in the corrected position;
   before digitally designing each bracket assembly, positioning a model straight wire archwire extending in a single plane and comprising at least one portion having a substantially continuous curvature relative to faces of a plurality of teeth in the digital representation;
   digitally designing each bracket assembly associated with the at least one portion by;
   digitally designing the base to conform to the face of the tooth to which the base is to be placed;
   digitally positioning the bracket relative to the model straight wire archwire such as to receive the at least one portion of the model archwire in the groove of the bracket without deformation of the substantially continuous curvature of the at least one portion of the model straight wire archwire; and
   after digitally designing the base and digitally positioning the bracket, digitally designing the intermediate component to extend between the bracket and the base; and
   producing each digitally designed bracket assembly.

2. The method of claim 1, wherein the device further comprises a treatment archwire homothetic to the model archwire, and the at least one groove of each bracket of the plurality of bracket assemblies is configured to receive the treatment straight wire archwire.

3. The method of claim 2, wherein the model straight wire archwire comprises a first potion having a substantially continuous curvature across incisors and canines of the dentition of the patient, and comprises second and third portions having a substantially continuous curvature across at least premolars of the dentition of the patient.

4. The method of claim 2, wherein the model straight wire archwire has a substantially continuous curvature over the entire length of the model straight wire archwire.

5. The method of claim 1, further comprising calculating the model straight wire archwire positioned in the digital representation.

6. The method of claim 2, wherein the model straight wire archwire comprises a plurality of portions of substantially continuous curvature and each of the plurality of portions of substantially continuous curvature is associated with the faces of a portion of the plurality of teeth in the digital representation, and the treatment archwire is homothetic to the model straight wire archwire on a portion-by-portion basis.

7. The method of claim 1, further comprising digitally merging the digitally designed base and intermediate component before producing each bracket assembly.

8. The method of claim 1, further comprising digitally designing the intermediate component with at least one positioning means on a contact surface thereof for positioning, the intermediate component relative to at least one of the base or bracket in the produced bracket assembly.

9. The method of claim 8, wherein the positioning means comprises a male or a female connection configured to mate with an opposed connection of at least one of the base or the bracket.

10. The method of claim 1, further comprising:
    positioning each produced digitally designed bracket assembly on a model of an arch of the teeth of the patient in pre-treatment positions; and
    forming a transfer channel about the positioned brackets and model, the transfer channel at least partially covers each bracket assembly.

11. The method of claim 1, wherein digitally positioning the bracket further comprises selecting a digital representation of a standard available bracket from a plurality of digital representations of orthodontic components.

12. The method of claim 11, wherein the selected standard digital representation is a digital representation of a standard available self-ligating bracket.

13. The method of claim 1, wherein digitally positioning the bracket comprises digitally positioning the bracket at a position adapted to carry out orthodontic treatment of the tooth and wherein digitally designing the intermediate component comprises digitally designing the intermediate component such that each bracket assembly corresponds to a geometry of a space between the face of the tooth to which the base is to be paced and the model straight wire archwire.

* * * * *

UNITED STATES PATENT AND TRADEMARK OFFICE
CERTIFICATE OF CORRECTION

PATENT NO.       : 8,944,811 B2
APPLICATION NO.  : 12/740354
DATED            : February 3, 2015
INVENTOR(S)      : Patrick Curiel and Daniel Julie Page 1 of 1

It is certified that error appears in the above-identified patent and that said Letters Patent is hereby corrected as shown below:

In the Claims,

In claim 13 at column 10, line 18 the word 'paced' should instead read --placed--.

Signed and Sealed this
Nineteenth Day of May, 2015

Michelle K. Lee
*Director of the United States Patent and Trademark Office*